United States Patent
Saito et al.

(10) Patent No.: US 7,770,232 B2
(45) Date of Patent: Aug. 3, 2010

(54) SCANNING PROBE MICROSCOPE SYSTEM

(75) Inventors: Akira Saito, Hyogo (JP); Masakazu Aono, Hyogo (JP); Yuji Kuwahara, Hyogo (JP); Jyunpei Maruyama, Hyogo (JP); Ken Manabe, Hyogo (JP)

(73) Assignee: Riken, Wako (JP)

( * ) Notice: Subject to any disclaimer, the term of this patent is extended or adjusted under 35 U.S.C. 154(b) by 245 days.

(21) Appl. No.: 11/887,276

(22) PCT Filed: Mar. 16, 2006

(86) PCT No.: PCT/JP2006/305203

§ 371 (c)(1),
(2), (4) Date: Nov. 26, 2007

(87) PCT Pub. No.: WO2006/103937

PCT Pub. Date: Oct. 5, 2006

(65) Prior Publication Data

US 2008/0258059 A1    Oct. 23, 2008

(30) Foreign Application Priority Data

Mar. 28, 2005   (JP) ............................. 2005-090396

(51) Int. Cl.
*G01Q 30/02* (2010.01)
(52) U.S. Cl. ............................. 850/9; 850/10; 850/26; 378/84; 378/145
(58) Field of Classification Search .................. 250/310; 850/9, 10, 26; 378/84, 145
See application file for complete search history.

(56) References Cited

U.S. PATENT DOCUMENTS 5,570,408 A * 10/1996 Gibson ....................... 378/145
5,898,176 A *  4/1999 Mori et al. ..................... 850/9

FOREIGN PATENT DOCUMENTS

| EP | 0 801 310 A1 | 10/1997 |
| JP | 8-178934 A | 7/1996 |
| JP | 10-282119 A | 10/1998 |
| JP | 2005-49186 A | 2/2005 |

(Continued)

OTHER PUBLICATIONS

"Mechanism of layer-by-layer Oxidation of Si(001) surfaces by two-dimensional Oxide-Island Nucleation of SiO2/Si Interfaces", Watanabe, H., Baba, T., Ichikawa, M., J. Journal of Phys. vol. 29, 2000, pp. 2015-2020.*

(Continued)

*Primary Examiner*—Jack I Berman
*Assistant Examiner*—Meenakshi S Sahu
(74) *Attorney, Agent, or Firm*—Birch, Stewart, Kolasch & Birch, LLP

(57) ABSTRACT

A scanning probe microscope system capable of identifying an element with atomic scale spatial resolution comprises: an X-ray irradiation means for irradiating a measurement object with high-brilliance monochromatic X-rays having a beam diameter smaller than 1 mm; a probe arranged to oppose to the measurement object; a processing means for detecting and processing a tunneling current through the probe; and a scanning probe microscope having an alignment means for relatively moving the measurement object, the probe, and the incident position of the high-brilliance monochromatic X-rays to the measurement object.

12 Claims, 7 Drawing Sheets

FOREIGN PATENT DOCUMENTS

WO  WO-96/20406 A1  7/1996

OTHER PUBLICATIONS

"EXAFS- and XANES-like Spectra obtained by X-ray excited Scanning Tunneling Microscope Tip Current Measurement" Tsuji, K.,Wagatsuma,K.,Sugiyama,K.,Hiraga,K.,Waseda,Y., Surface and Interface Analysis vol. 27, 1999, pp. 132-135.*

Maruyama, "Hoshako STM Sochi o Mochiita Handotai Hyomen to Kokido X-sen tono Sogo Sayo no Kaiseki," 2004 Nen (Heisei 16 Nen) Shunki Dai 51 Kai Oyo Butsurigaku Kankei Rengo Koenkai Koen Yokoshu, vol. 2, 2004, pp. 726.

Matsushima, "Development and trial measurement of synchrotron-radiation-light-illuminated scanning tunneling microscope," Review of Scientific Instruments, vol. 75, No. 6, 2004, pp. 2149-2153.

Kuwabara, "Ryoshi Nano Zairyo Kenkyu Team," Heisei 14 Nendo Annual Reports of Research Activities, Institute of Physical and Chemical Research, 2003, pp. 1309-1310.

Manabe, "Hoshako STM Sochi o Mochiita Jikkukan Genshi Scale deno Genso Shikibetsu eno Kokoromi," 2005 Nen (Heisei 17 Nen) Shunki Dai 52 Kai Oyo Butsurigaku Kankei Rengo Koenkai Koen Yokoshu, vol. 2, 2005, pp. 777.

K. Tsuji et al., Jpn. J. Appl. Phys., 37, L1271-1273 (1998).

* cited by examiner

SCANNING PROBE MICROSCOPE SYSTEM

TECHNICAL FIELD

The present invention relates to a Scanning Probe Microscope (SPM) system, and more particularly to a scanning probe microscope system wherein a microscopy for scanning a microprobe represented by Scanning Tunneling Microscope (STM) or Atomic Force Microscope (AFM) is applied.

BACKGROUND TECHNOLOGY

Most of conventional nanostructure evaluation techniques are concerned only to the one which provides limited individual information. A nanostructure itself has been construed by judging synthetically the individual information obtained respectively from a plurality of nanostructure evaluation techniques.

Among these conventional nanostructure evaluation techniques, since a scanning probe microscope system has atomic scale spatial resolution so that spatial information can be obtained, such scanning probe microscope system may be applied also to the observation for a system exhibiting no periodicity. As a result, the scanning probe microscope system has contributed remarkably to the contemporary development of nanoscience.

However, the scanning probe microscope system has involved such a problem that an element cannot be identified.

In view of the above-described problem, a variety of trials for elementary analysis with atomic scale spatial resolution has been proposed from viewpoints of electronic state, vibrational state or electrostatic capacity and the like. However, the actual examples wherein elementary analysis is carried out have been insensibly reported only in respect of the measuring objects and conditions of very limited particular materials. Accordingly, the actual examples have not been as a general technique.

On one hand, a technique wherein X-rays are applied is proposed as a technique for affording elementary selectivity to a scanning probe microscope. The technique is the one wherein X-rays are irradiated on a measurement object to cause inner shell excitation selective for the specified atomic species under observation by means of the scanning probe microscope, whereby the inner shell excitation caused is intended for observation (see the non-patent literary document 1).

However, since the technique wherein X-rays are applied exhibits poor excitation efficiency, it has been pointed out that the remarkable increase in the photon density of incident radiation is desired.

In view of such pointing out, an example wherein synchrotron orbital radiation being a high brilliance light source is applied has been recently reported as a technique for increasing remarkably the photon density of incident radiation (see non-patent literary document 2).

In the techniques disclosed in the above-described non-patent literary documents 1 and 2, since the X-rays having a beam diameter of about $\phi 1$ to several mm or so are irradiated to a measurement object, it results in a broad area wherein the irradiation area of X-rays in the measurement object has a diameter of about $\phi 1$ to several mm or so. Besides, the techniques are arranged in such that the emission electron from a specified element which has been excited is captured by using the probe of a scanning probe microscope as a collector for the emission electron.

Accordingly, there is such a problem that electrons generated in a wide range are collected in accordance with the techniques disclosed in the non-patent literary documents 1 and 2, so that the spatial resolution stays in an order of 10 μm. Such problem is a principle problem impartible with respect to such conventional technique, so that it is very difficult to obtain atomic scale spatial resolution. In these circumstances, there is no way to establish a technique which is very difficult to achieve, an example of the difficult technique is such that only several nm of the extreme end of the probe of a scanning probe microscope is merely made of a conductor, and the other part thereof is coated with an insulating material in order to elevate spatial resolution for applying such conventional technique as described above.

Non-patent literary document 1: K. Tsuji et al., Jpn. J. Appl. Phys., 37, L 1271-1273 (1998)

Non-patent literary document 2: T Matsushima et al., Rev. Sci. Instrum., 75, (2004) 2149

DISCLOSURE OF THE INVENTION

Problems to be Solved by the Invention

The present invention has been made in view of the problems as described above in reference to the prior art, and an object of the invention is to provide a scanning probe microscope system capable of identifying an element with atomic scale spatial resolution.

Means for Solving the Problems

In order to achieve the above-described object, the present invention has constituted a scanning probe microscope system having a very good S/N ratio and obtained by combining an X-ray irradiation means for irradiating high-brilliance monochromatic X-rays having a small beam diameter at a constant incidence angle with a scanning probe microscope.

Namely, according to the scanning probe microscope system of the present invention, it becomes possible to achieve the observation with atomic scale and the constitution of a nanostructure while identifying a specified element. The scanning probe microscope system is obtained by combining a scanning probe microscope with the high-brilliance monochromatic X-rays capable of inner shell excitation selective to a specified element.

Furthermore, in the scanning probe microscope system of the present invention, a small diameter beam wherein the beam diameter of high-brilliance monochromatic X-rays has been reduced is used in order to obtain a high S/N ratio.

Moreover, the scanning probe microscope system according to the present invention is arranged in such that the beam having a small diameter of the high-brilliance monochromatic X-rays can be matched with the position immediately below the observation point of the scanning probe microscope at short times.

Namely, the scanning probe microscope system according to the present invention includes an X-ray irradiation means for irradiating a measurement object with high-brilliance monochromatic X-rays having a beam diameter smaller than 1 mm; and a scanning probe microscope having a probe arranged to oppose to the above-described measurement object, a processing means for detecting and processing a tunneling current through the above-described probe, and an alignment means for relatively moving the above-described measurement object, the above-described probe, and the incident position of the above-described high-brilliance monochromatic X-rays to the measurement object.

Moreover, in the scanning probe microscope system of the above-described invention, the above-described X-ray irradiation means irradiates the high-brilliance monochromatic X-rays the wavelength of which is matched with the absorption edge of a desired element.

Still further, in the scanning probe microscope system of the above-described invention, the beam diameter of the high-brilliance monochromatic X-rays irradiated from the above-described X-ray irradiation means is 1 μm or more to 100 μm or less.

Yet further, in the scanning probe microscope system of the above-described invention, the above-described X-ray irradiation means irradiates the high-brilliance monochromatic X-rays in total reflection condition with respect to the above-described measurement object.

Furthermore, in the scanning probe microscope system of the above-described invention, the above-described alignment means includes a θ-stage having the rotating plane parallel to the horizontal plane in an XYZ-orthogonal coordinate system to control the incidence angle of the high-brilliance monochromatic X-rays irradiated from the above-described X-ray irradiation means with respect to the above-described measurement object, an Xt-stage for controlling the movement towards an X-axial direction in the XYZ-orthogonal coordinate system to match the extreme end of the above-described probe with the rotating center of the above-described θ-stage, a Zt-stage for controlling the movement towards a Z-axial direction in the XYZ-orthogonal coordinate system to match the extreme end of the above-described probe with the rotating center of the above-described θ-stage, a Zb-stage for controlling the movement towards the Z-axial direction in the XYZ-orthogonal coordinate system to match the above-described rotating center of the θ-stage with the beam position of the high-brilliance X-rays irradiated from the above-described X-ray irradiation means, and a Yb-stage for controlling the movement towards the Y-axial direction in the XYZ-orthogonal coordinate system to match the height of the observation point of the above-described measurement object immediately below the above-described probe with the beam position of the high-brilliance monochromatic X-rays.

In addition, the scanning probe microscope system in the above-described invention includes further a monitoring means for monitoring the vicinities of the observation point on the above-described measurement object immediately below the above-described probe.

Moreover, in the scanning probe microscope system of the above-described invention, the above-described monitoring means includes an aperture member positioned at the uppermost stream with respect to the beam traveling direction of the high-brilliance monochromatic X-rays irradiated from the above-described X-ray irradiation means and provided with at least one pinhole for reducing the beam diameter to a diameter smaller than 1 mm, an ion chamber for monitoring the beam intensity of the beam of the high-brilliance monochromatic X-rays passed through the pinhole of the above-described aperture member, an absorption plate for absorbing the high-brilliance monochromatic X-rays irradiated to the above-described measurement object to decrease the beam intensity, a screen to which the high-brilliance monochromatic X-rays passed through the above-described absorption plate are irradiated, whereby the positional relationship among the above-described probe, the above-described measurement object, and the beam position of the above-described high-brilliance monochromatic X-rays is projected on the screen in the form of a shadowgraph, a optical microscope system for amplifying the above-described shadowgraph projected on the screen, a CCD camera for taking the shadowgraph amplified by the above-described optical microscope system, a reflecting mirror for reflecting the above-described shadowgraph on the screen to input to the above-described CCD camera, and a semiconductor analyzer for counting the yield point of the fluorescence X-rays emitted from the above-described measurement object and the above-described probe to analyze the energy.

Still further, in the scanning probe microscope system of the above-described invention, the above-described probe is coated with an insulating material other than the extreme end thereof.

Yet further, in the scanning probe microscope system of the above-described invention, the above-described probe is composed of carbon nanotube.

Besides, in the scanning probe microscope system of the above-described invention, it is operated in an ultra-high vacuum environment.

ADVANTAGEOUS EFFECTS OF THE INVENTION

Since the present invention is constructed as described above, it results in such excellent advantages that an observation by means of atomic scale spatial resolution becomes possible while identifying an element, and it is possible to establish a nanostructure.

Figure 1:
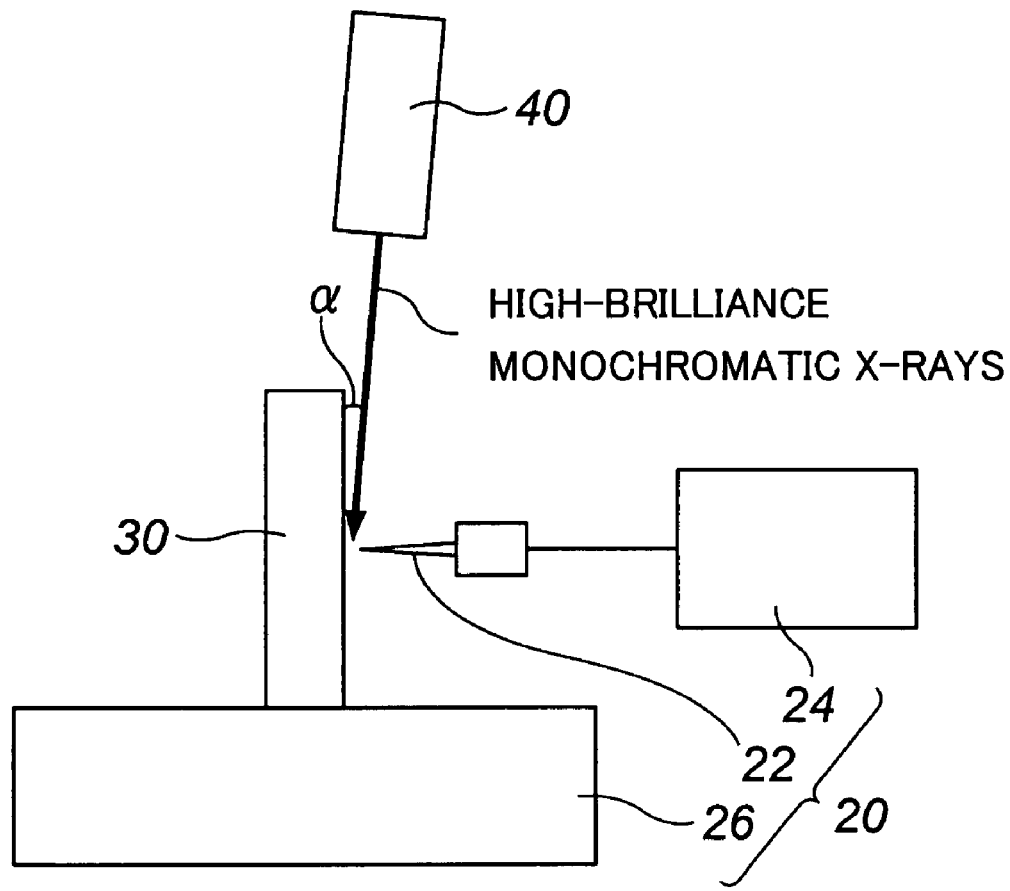
FIG. 1 is a conceptual, constitutional, explanatory diagram showing the principle of the scanning probe microscope according to an example of an embodiment of the present invention.

EXPLANATION OF REFERENCE NUMERALS 10 scanning probe microscope system
20 scanning probe microscope
22 probe
24 processing system
26 alignment mechanism
26a θ stage
26b Xt stage
26c Zt stage
26d Zb stage
26e Yb stage
30 sample
40 X-ray irradiation mechanism
42 monitoring mechanism
42a aperture member
42a-1, 42a-2, 42a-3, 42a-4, 42a-5, 42a-6 pinhole
42b ion chamber
42c absorption plate 42d screen
42e optical microscope system
42f CCD camera
42g reflecting mirror
42h semiconductor analyzer

THE BEST MODE FOR EMBODYING THE INVENTION

In the following, an example of the embodiment of the scanning probe microscope system according to the present invention will be described in detail by referring to the accompanying drawings.

FIG. 1 is a conceptual, constitutional, explanatory diagram showing the principle of the scanning probe microscope according to an example of an embodiment of the present invention.

The scanning probe microscope system 10 comprises a scanning probe microscope 20 including a probe 22 opposed to a sample 30 being a measurement object, processing means 24 for detecting and processing a physical quantity through the probe 22, and an alignment mechanism 26 (wherein the alignment mechanism 26 will be mentioned later by referring to FIG. 2. In the embodiment, the alignment mechanism 26 makes the sample 30 to be moved with respect to the probe 22 and the incident position of the beam of the high-brilliance monochromatic X-rays, whereby the relative movement of the sample 30, the probe 22, and the incident position of the beam of the high-brilliance monochromatic X-rays is realized.) for relatively moving the sample 30, the probe 22, and the incident position of the beam of the high-brilliance monochromatic X-rays (which will be mentioned later) to the sample 30; and X-ray irradiation mechanism 40 for irradiating the high-brilliance monochromatic X-rays to the sample 30. It is to be noted that such a point that a physical quantity is detected through the probe 22 of the scanning probe microscope 20, and the physical quantity detected is processed by the processing means 24 is the same as that which is well-known heretofore, so that the prior art can be used. Accordingly, the detailed constitution and the functions thereof are omitted optionally.

In the scanning probe microscope system 10, the high-brilliance monochromatic X-rays wherein the scanning probe microscope system is allowed to fit, to the absorption edge of the intended element the wavelength of which is desired to measure are input to the observation point (point of measurement) of the sample 30 in the scanning probe microscope 20 from the X-ray irradiation mechanism 40. In this case, the beam diameter of the high-brilliance monochromatic X-rays irradiated to the observation point by means of the X-ray irradiation mechanism 40 is reduced smaller diameter than that of 1 mm, for example, up to about $\phi 10$ μm or so (preferable is $\phi 10$ μm). (In this respect, the beam diameter of X-rays in a conventional art is $\phi 1$ to several mm as described above.)

Moreover, an incidence angle α of the high-brilliance monochromatic X-rays irradiated from the X-ray irradiation mechanism 40 to the sample 30 is made to be acute, for example, up to about 0.1 degree or so, thereby to establish total reflection condition. As described herein, when the incidence angle α of the high-brilliance monochromatic X-rays irradiated from the X-ray irradiation mechanism 40 to the sample 30 is made to be acute thereby to establish the total reflection condition, the high-brilliance monochromatic X-rays irradiated from the X-ray irradiation mechanism 40 do not invade deeply into the sample 30.

In other words, when such arrangement that the beam diameter of high-brilliance monochromatic X-rays is reduced smaller as well as such arrangement that an incidence angle α thereof to the sample 30 is made to be acute thereby to obtain total reflection condition are applied, it becomes possible to reduce extra X-rays to be applied to the sample 30 due to the point of the dimension of the beam diameter and the point of the invasion depth of the X-rays into the sample 30.

As a result of reducing smaller the beam diameter of the high-brilliance monochromatic X-rays and making the incidence angle α to be acute with respect to the sample 30 to obtain total reflection condition, it becomes possible to prevent the emission of electron from a wide region where the spatial resolution due to the irradiation of the X-rays a beam diameter of which is about $\phi 1$ to several mm or so onto the sample 30 is impaired which has been a problem in the prior art. Furthermore, it becomes possible to remove the thermal influence due to the application of a high-brilliance light (for example, instability in a measurement system represented by a drift between a probe and a sample).

As a light source in the X-ray irradiation mechanism 40, for example, the beam line (BL) of synchrotron radiation SPring-8 is applicable.

Moreover, the X-ray irradiation mechanism 40 is provided with a monitoring mechanism 42 which becomes possible to monitor the vicinities of the observation point on the sample 30 immediately below the probe 22, whereby the high-brilliance monochromatic X-rays having a minute beam diameter of about $\phi 10$ μm or so can be precisely focused to the observation point on the sample 30 immediately below the probe 22 in ultra-high vacuum by means of the alignment mechanism 26 for a short period of time while controlling angularly the X-rays (the monitoring mechanism 42 will be described in detail hereinbelow by referring to FIG. 3).

Furthermore, the probe of a scanning probe microscope has been used as an emission electron collector in the conventional art, whereby the emission electron from an excited specified element has been obtained. However, when an emission electron is used as its signal as described above, the emission area of the emission electron extends over around 10 μm, even if the beam diameter of the high-brilliance monochromatic X-rays irradiated from the X-ray irradiation mechanism 40 is reduced smaller up to about $\phi 10$ μm or so. Accordingly, there is such a fear that it is difficult to obtain atomic scale spatial resolution. In this case, however, when the beam diameter is reduced smaller than about $\phi 10$ μm or so, there is such a fear that it becomes difficult to achieve the alignment with respect to the observation point on the sample 30.

For this reason, it is arranged in such that not emission electron, but the change of state in the vicinity of Fermi energy generated by inner shell excitation is captured as the change of intensity of tunneling current in the scanning probe microscope system 10. In other words, the scanning probe microscope system 10 does not collect an emission electron by means of the probe 22, but the changes in the tunneling current itself produced by such a manner that high-brilliance monochromatic X-ray energy steps over the absorption edge of a specified element are measured as the physical quantity.

As mentioned above, in the scanning probe microscope system 10, high-brilliance monochromatic X-rays are used, the beam diameter of the high-brilliance monochromatic X-rays is reduced smaller, whereby its S/N ratio is remarkably elevated, and further, not emission electron, but the changes (finite difference) in tunneling current are captured as the physical quantity, and as a result, the condition of a material surface/the composition analysis are conducted with atomic scale spatial resolution.

Accordingly, when the scanning probe microscope system 10 is used, not only the observation of a material surface can be made, but also the production of a nanostructure becomes possible by using both of probe bias and high-brilliance monochromatic X-ray excitation thereby to control local reactions.

In order to increase an S/N ratio of signal, it is required to remove an extra emission electron to be introduced to the probe 22 as much as possible. For this reason, it is desired that a part other than the extreme end of the probe 22 is coated with an insulating material, and that a material having a very high aspect ratio such as a carbon nanotube is used as the probe 22.

Figure 2:
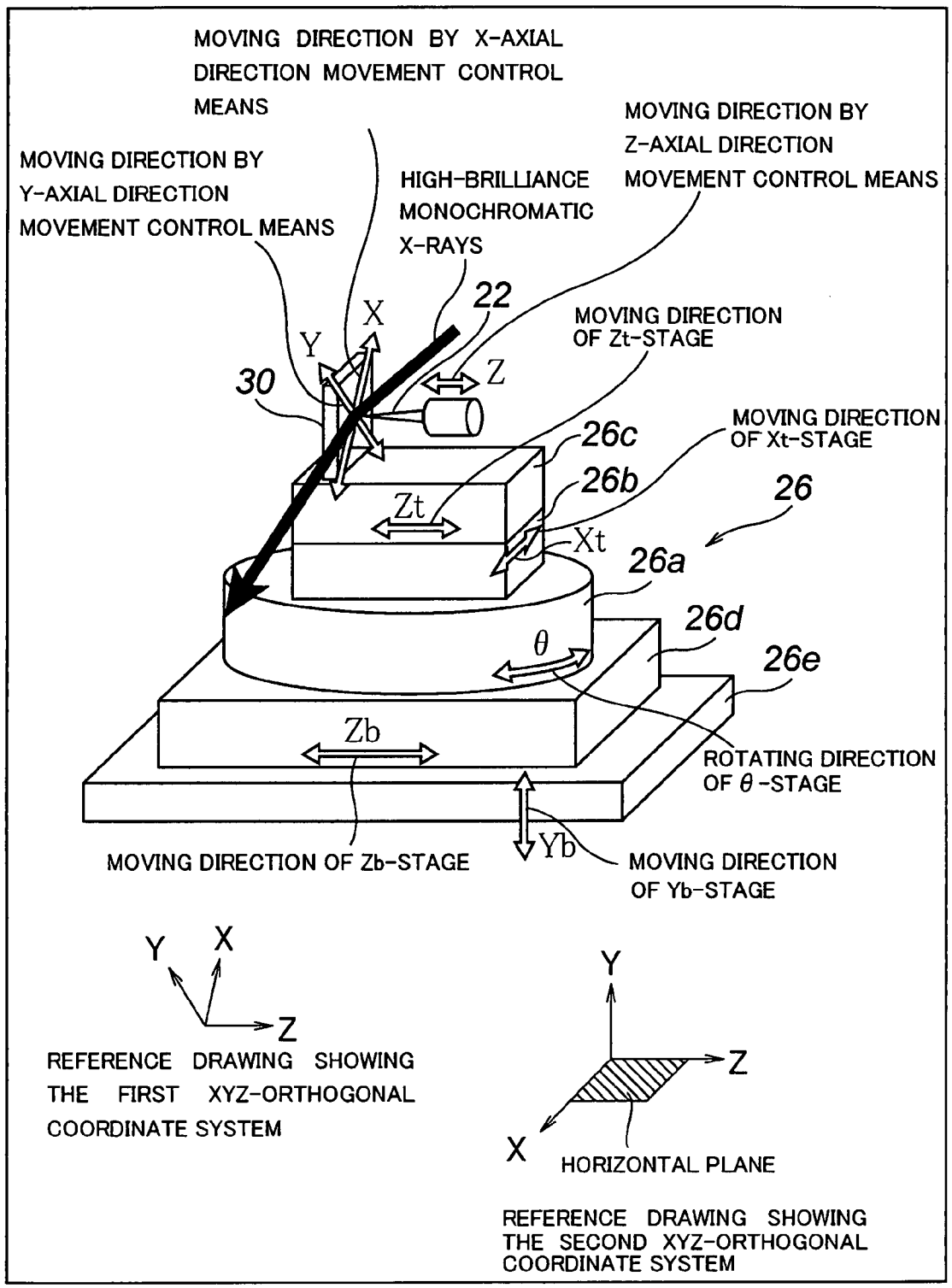
FIG. 2 is a conceptual, constitutional, explanatory view showing a alignment mechanism.
Figure 3:
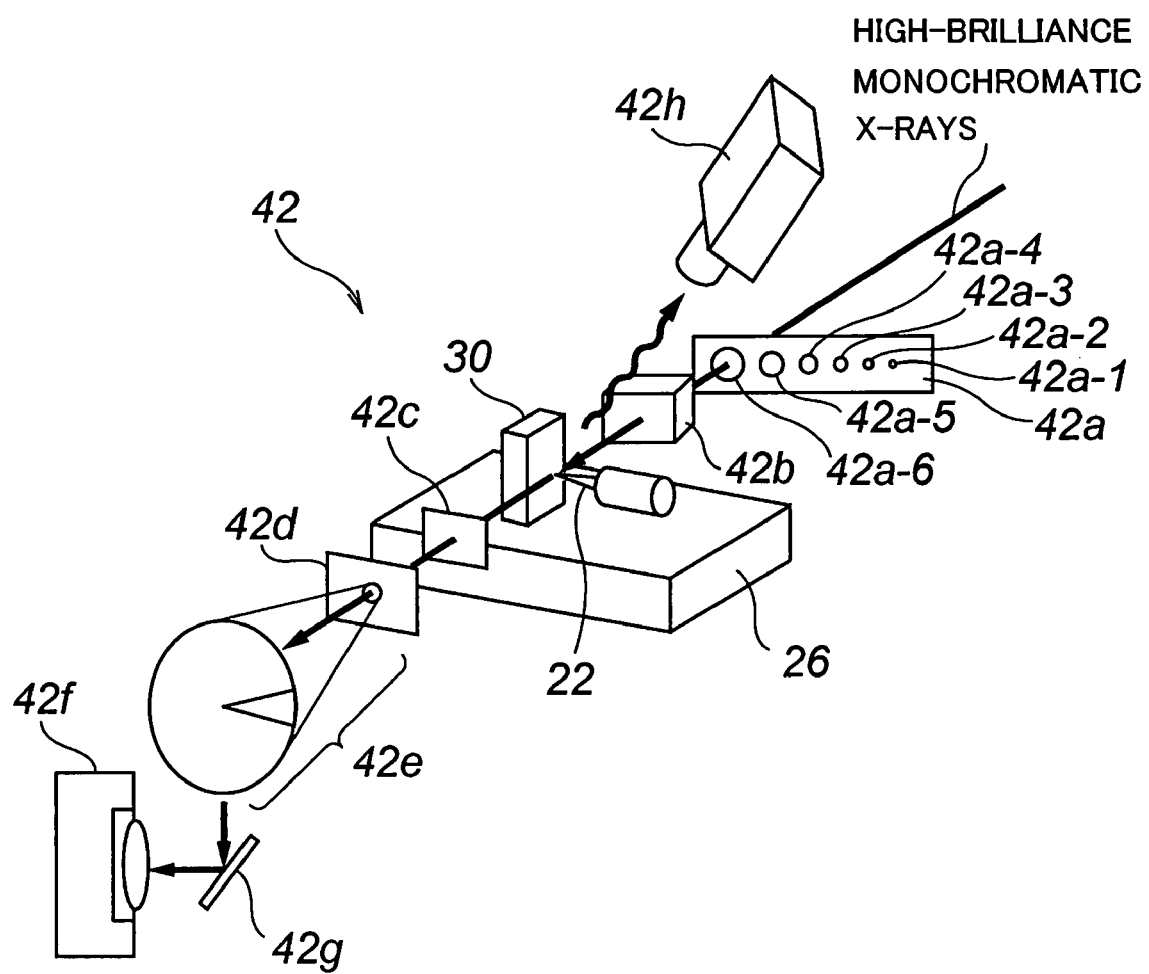
FIG. 3 is a conceptual, constitutional, explanatory view showing a monitoring mechanism.

FIG. 2 is a conceptual, constitutional, explanatory view showing an alignment mechanism 26, and FIG. 3 is a conceptual, constitutional, explanatory view showing a monitoring mechanism 42.

The alignment mechanism 26 is provided with an X-axial direction movement control means (not shown), which has been heretofore well-known, for controlling the movement along the X-axial direction in a first XYZ-orthogonal coordinate system (see the reference drawing showing the first XYZ-orthogonal coordinate system in FIG. 2), a Y-axial direction movement control means (not shown), which has been heretofore well-known, for controlling the movement along the Y-axial direction in the first XYZ-orthogonal coordinate system, and a Z-axial direction movement control means (not shown), which has been heretofore well-known, for controlling the movement along the Z-axial direction in the first XYZ-orthogonal coordinate system as in a conventional scanning probe microscope.

In addition, the alignment mechanism 26 is comprised of, as a novel constitution which has never been in a conventional art, a θ-stage 26a having a rotating plane surface in parallel to the horizontal plane in a second XYZ-orthogonal coordinate system (see the reference drawing showing the second XYZ-orthogonal coordinate system in FIG. 2) to control an incidence angle α of the high-brilliance monochromatic X-rays irradiated from the X-ray irradiation mechanism 40 with respect to the sample 30, an Xt stage 26b for controlling the movement of the probe 22 towards the X-axial direction in the second XYZ-orthogonal coordinate system to allow the extreme end of the probe 22 to match with the rotating center of the θ-stage 26a, a Zt stage 26c for controlling the movement of the probe 22 towards the Z-axial direction in the second XYZ-orthogonal coordinate system to allow the extreme end of the probe 22 to match with the rotating center of the θ-stage 26a, Zb-stage 26d for controlling the movement towards the Z-axial direction in the second XYZ-orthogonal coordinate system to allow the rotating center of the θ-stage 26a to match with the beam position of the high-brilliance monochromatic X-rays irradiated from the X-ray irradiation mechanism 40, and a Yb-stage 26e for controlling the movement towards the Y-axial direction in the second XYZ-orthogonal coordinate system to allow the height of an observation point of the sample 30 immediately below the probe 22 to match with the beam position of high-brilliance monochromatic X-rays.

On one hand, the monitoring mechanism 42 is comprised of an aperture member 42a on which six pinholes 42a-1, 42a-2, 42a-3, 42a-4, 42a-5, and 42a-6 each having a different diameter are provided in a line under the condition in which the positions of the six pinholes can be controlled so as to be capable of gradual beam positioning wherein the pinhole 42a-1 is positioned in the uppermost stream with respect to the beam travelling direction of the high-brilliance monochromatic X-rays to reduce the beam diameter to φ10 μm; an ion chamber 42b for monitoring the beam intensity of the high-brilliance monochromatic X-rays which pass through any of the six pinholes 42a-1, 42a-2, 42a-3, 42a-4, 42a-5, and 42a-6 of the aperture member 42a; an absorption plate 42c for absorbing the high-brilliance monochromatic X-rays irradiated on the sample 30 to decrease the beam intensity; a screen 42d to which the high-brilliance monochromatic X-rays passed through the absorption plate 42c are irradiated, whereby a positional relationship among the probe 22, the sample 30, and the beam position of the high-brilliance monochromatic X-rays is projected thereto in the form of a shadowgraph; an optical microscope system (the optical microscope system in the embodiment has a magnifying power of up to 800 times) 42e for amplifying the shadowgraph projected on the screen 42d; a CCD camera 42f for taking the shadowgraph amplified by the optical microscope system 42e; a reflecting mirror 42g for reflecting the shadowgraph on the screen 42d to input the same to the CCD camera 42f; and a semiconductor analyzer (SDD) 42h for counting the yield point of the fluorescence X-rays emitted from the sample 30 and the probe 22 to make energy analysis.

In the constitution as described above, the alignment probe microscope system 10 is preferably operated under ultra-high vacuum environment wherein when high-brilliance monochromatic X-rays are irradiated from the light source of the X-ray irradiation mechanism 40, the high-brilliance monochromatic X-rays pass through any of the six pinholes 42a-1, 42a-2, 42a-3, 42a-4, 42a-5, and 42a-6 on the aperture member 42a, and the beam intensity thereof is monitored in the ion chamber 42b.

Thereafter, the positional relationship among the probe 22, the sample 30, and the beam position of the high-brilliance monochromatic X-rays is projected on the downstream screen 42d in the form of a shadowgraph, the shadowgraph is further amplified by the microscope system 42e, and the amplified shadowgraph is reflected by the reflecting mirror 42g to be taken by the most downstream CCD camera 42f.

Thus, the positioning alignment of the high-brilliance monochromatic X-ray beam to the observation point on the sample 30 immediate below the probe 22 can be rapidly achieved in real time by means of the alignment mechanism 26 shown in FIG. 2 while watching the shadowgraph projected on the screen 42d.

Furthermore, the semiconductor analyzer 42h counts the yield point of the fluorescence X-ray emitted from the sample 30 and the probe 22, and conducts further energy analysis, whereby it is possible to confirm the adatoms on the surface of the sample 30 which are excited by high-brilliance monochromatic X-rays and types of the elements of probe 22.

In the present embodiment, although the absorption plate 42c is provided on the upstream of the screen 42d for decreasing the damage of the screen 42d, such absorption plate 42c may not be provided dependent on the brilliance of incident radiation, as a matter of course.

Moreover, not only a fluorescence powder having a large particle diameter is used, but fluorescent crystal having a high density is used in the screen 42d itself in the present embodiment so as to be possible to observe the interior of a region wherein the diameter is around φ10 μm.

In addition, it is arranged in the present embodiment in such that the image of the shadowgraph is guided to a different height from that of the beam of the high-brilliance monochromatic X-rays through the reflecting mirror 42g so as the high-brilliance monochromatic X-rays not to be input directly to the CCD camera 42f.

Next, an experiment carried out by the inventor of this application with the use of the scanning probe microscope system 10 according to the present invention will be described. First, FIGS. 4(a), 4(b), and 4(c) are explanatory views each showing a condition of the shadowgraph observed actually by the inventor of this application.

Figures 4A, 4B, 4C:
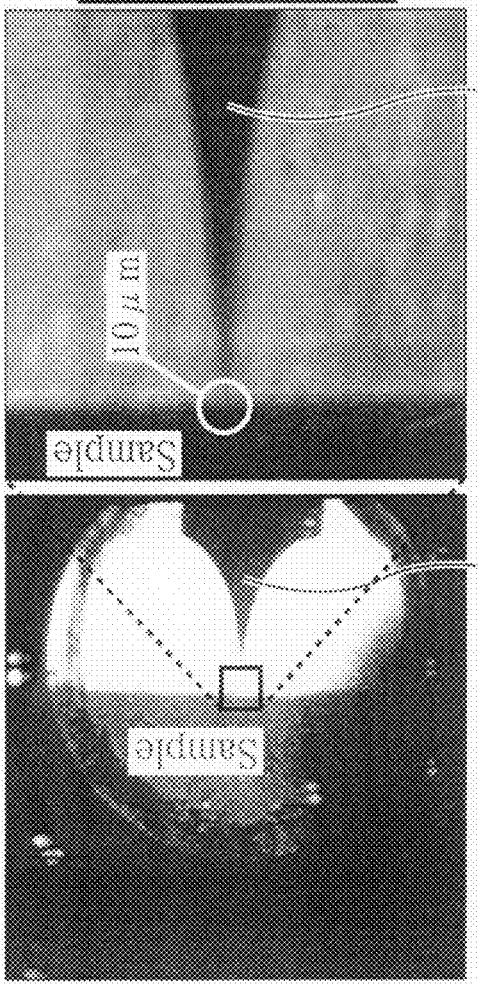
FIGS. 4(a), 4(b), and 4(c) are explanatory views each showing the condition of a shadowgraph observed actually by the inventor of this application.

FIGS. 4(a) and 4(b) are views each showing a condition wherein the beam of high-brilliance monochromatic X-rays is allowed to pass through the pinhole having φ800 μm diameter among the six pinholes 42a-1, 42a-2, 42a-3, 42a-4, 42a-5, and 42a-6 on the aperture member 42a, i.e. the beam of high-brilliance monochromatic X-rays having φ800 μm diameter is irradiated to the sample 30 in order to implement the rough positioning of the observation point of the sample 30 immediately below the probe 22 with respect to the beam position of the high-brilliance monochromatic X-rays. Further, FIG. 4(a) is a view showing the condition wherein the shadowgraph is amplified 300 times by means of the optical microscope system 42e; and FIG. 4(b) is a view showing the condition wherein the shadowgraph is amplified 800 times by means of the optical microscope system 42e.

When it is arranged in such that the aperture member 42a is moved, whereby the beam of high-brilliance monochromatic X-rays is allowed to pass through the pinhole having φ10 μm diameter among the six pinholes 42a-1, 42a-2, 42a-3, 42a-4, 42a-5, and 42a-6 while maintaining the condition of the 800 times high magnifying power shown in FIG. 4(b) so that the beam of the high-brilliance monochromatic X-rays having φ10 μm diameter is irradiated on the sample 30, the high precise positioning of the observation point of the sample 30 immediate below the probe 22 with respect to the beam position of the high-brilliance monochromatic X-rays can be achieved as shown in FIG. 4(c).

In addition, the reflection spot of total reflection is recognized in FIG. 4(c) wherein it is understood that both of the incidence angle and the beam position of high-brilliance monochromatic X-rays is in an ideal condition.

In accordance with the experiment by the inventor of this application, about two hours are required for a period of time from starting a machine time to the condition shown in FIG. 4(c) as a result of applying the scanning probe microscope system 10 according to the present invention. It may be understood that a very efficient position control can be made with taking such fact that the high-brilliance monochromatic X-rays having φ10 μm beam diameter which cannot be visually observed are positioned with respect to the observation point of the sample 30 immediately below the probe 22.

Besides, the inventor of this application has tried to fabricate a Ge nano-inland having a film thickness of 0.3 ML on the clean surface of a Si (111) substrate, to conduct the positioning of the observation point in the condition as shown in FIG. 4(c), and to discriminate Si from Ge being heterogeneous elements existing mixedly on the Si substrate surface at the observation point.

Figure 5:
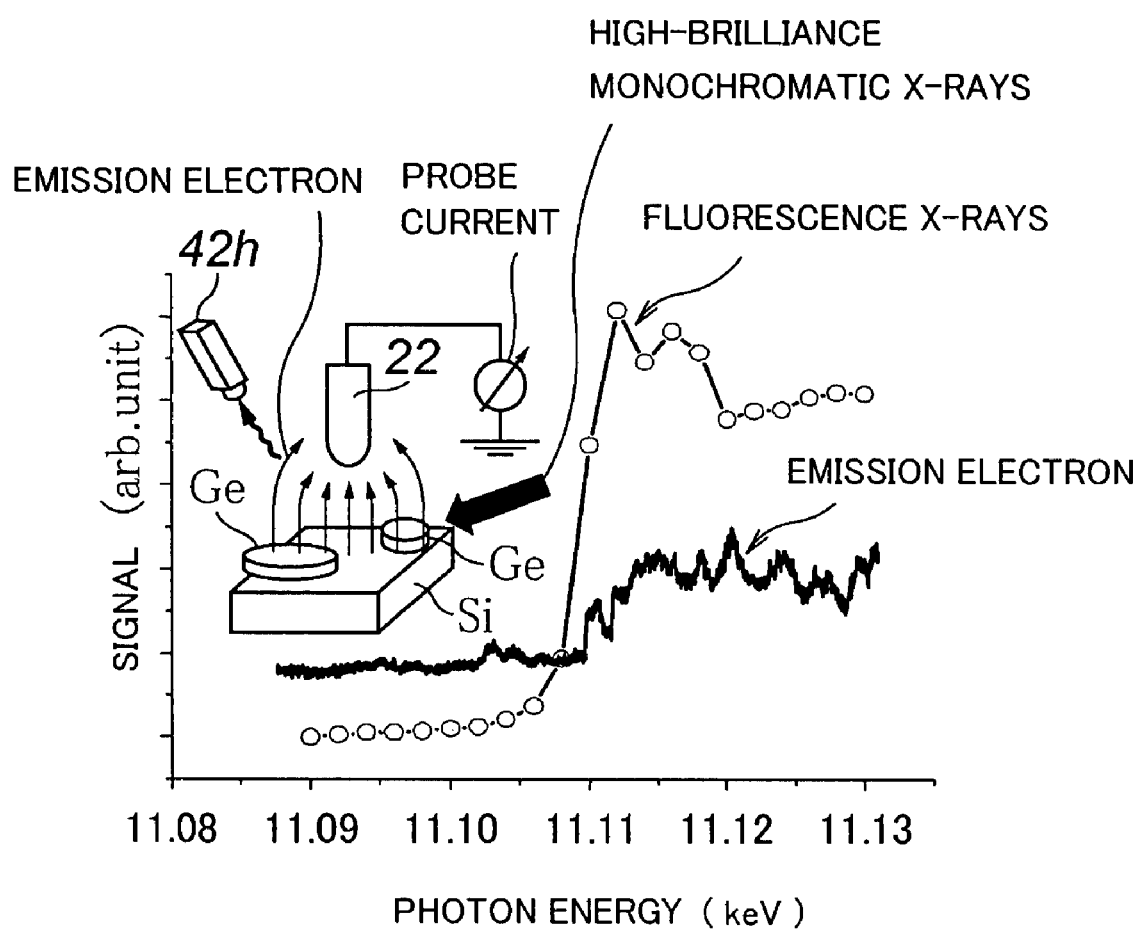
FIG. 5 is a graph showing an energy dependency of fluorescence X-ray and emission electrons.

First, a measurement was conducted in such that the probe 22 was made to be more apart from the sample 30 than that in a tunneling condition (all the signals were emission electrons) as shown in the non-patent literary document 1. In FIG. 5, the energy dependency of the emission electrons thus obtained is shown. Besides, in FIG. 5, the fluorescence X-ray profile from the semiconductor analyzer 42h (which has been already established as fluorescence XAFS, and the justness thereof has been proved.) is indicated as a reference.

According to FIG. 5, the increase is recognized also in the emission electrons at the K-absorption edge of Ge (11.11 keV) observed in the semiconductor analyzer 42h, so that it is understood that the detection of the minute emission electrons from an ultrathin Ge of 0.3 ML is possible by means of the scanning probe microscope system 10. It is, however, difficult to obtain high spatial resolution without any arrangement, because emission electrons are measured in a wide range as mentioned in the prior art.

Figure 6:
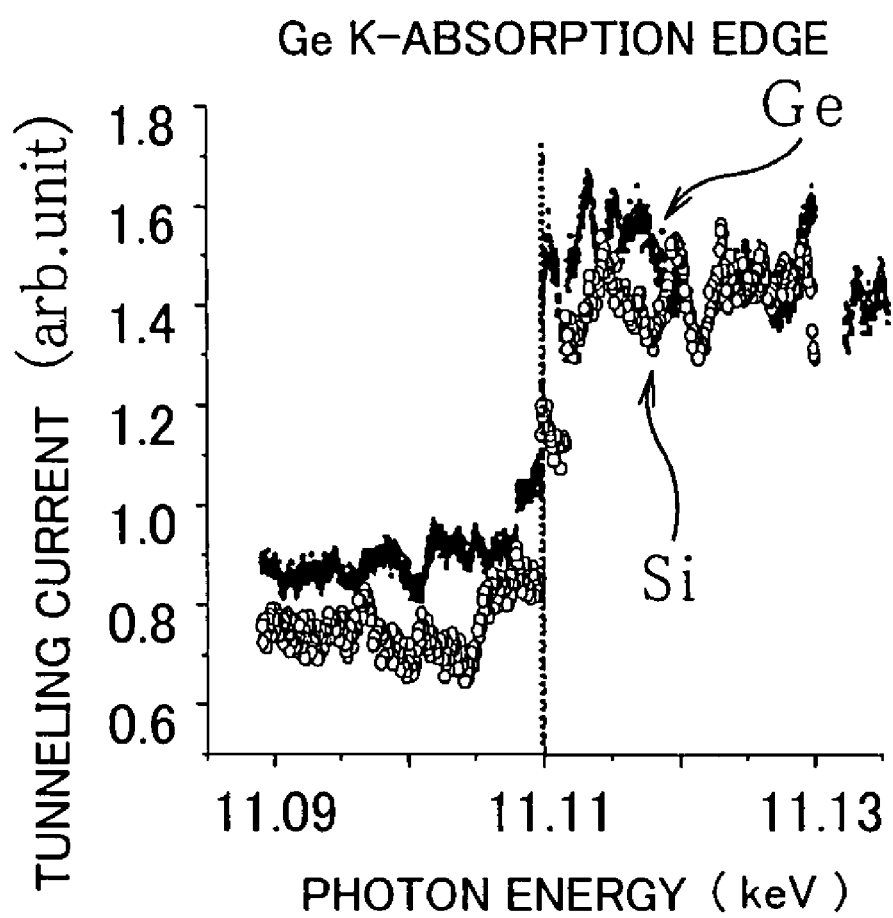
FIG. 6 is a graph showing an energy dependency of tunneling current on Si and Ge.
Figure 7:
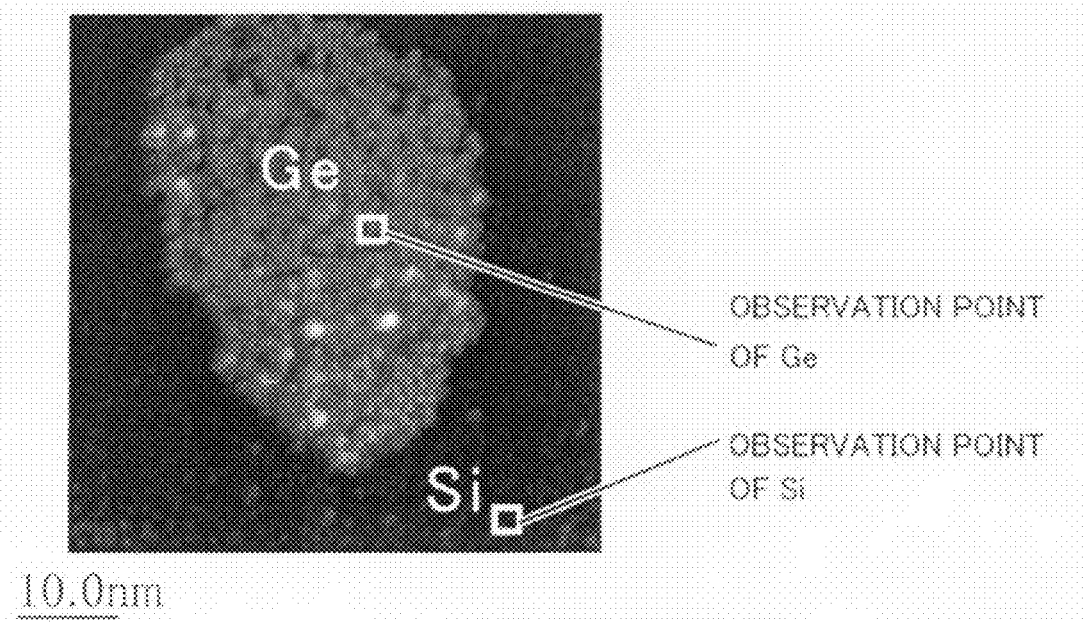
FIG. 7 is an explanatory view showing a state wherein each observation point of Ge and Si at the time when the graph shown in FIG. 6 is obtained is expressed, and the state of which is obtained by means of a scanning tunneling microscope.

Under the circumstances, it is arranged in the scanning probe microscope system 10 in such that the probe 22 is made to be near to the sample 30 to be in a tunneling condition, and the energy dependency of tunneling current is measured. The results measured are shown in FIG. 6 (the tunneling current is added to signals). Further, in FIG. 6, the profiles of the tunneling currents in the respective observation points of Ge and Si in the scanning tunneling microscopic appearances shown in FIG. 7 are indicated. Clearer steps are observed in the profiles of the tunneling currents shown in FIG. 6 than that of the emission electrons shown in FIG. 5 wherein it is understood that new current components are added in comparison with that of FIG. 5.

Therefore, remarkable improvements are recognized in comparison with that of the prior art.

Moreover, there are differences on the Si and the Ge in the profiles. Namely, the Si has a higher step of the profile than that of the Ge. In other words, the fact to the effect that such differences are observed between different elements in spite of the condition wherein the observation point of these elements are distant only about 20 nm from one another as shown in FIG. 7 means that the spatial resolution for discriminating elements are remarkably improved up to around 10 nm (about 1000 times higher) in comparison with around 10 μm of the prior art.

As explained above, the scanning probe microscope system 10 makes possible to input the high-brilliance monochromatic X-rays which have been matched with the absorption edge of a specified element to the observation point of the scanning probe microscope 20, whereby the identification of elements becomes possible.

Furthermore, it is arranged in such that the beam diameter of the high-brilliance monochromatic X-rays to be input to the sample 30 are reduced to φ10 μm, and further the incident angle α of the high-brilliance monochromatic X-rays to be input to the sample 30 is made to be acute up to 0.1° thereby to establish a total reflection condition in the scanning probe microscope system 10, whereby the extra X-rays to be input to the sample 30 is reduced from the viewpoint of a beam size and that of an intrusion depth. As a result, emission of electron can be prevented from a wide range of from 1 to several mm diameter as in the prior art which damages spatial resolution while even increasing the inner shell excitation efficiency immediately below the probe 22 by applying high-brilliance X-rays. In addition, instability in a measuring system represented by thermal drift comes to be removable.

Moreover, in even the case where the beam line (BL) of the SPring-8 of a Synchrotron Radiation Facility is used as the light source in the X-ray irradiation mechanism 40, it becomes possible to match the high-brilliance monochromatic X-rays having a beam diameter of around φ10 μm with the observation point on the sample 30 immediately below the probe 22 in high precision at short times while controlling the angles in the ultra-high vacuum of the Synchrotron Radiation Facility.

Besides, even the beam of X-rays is reduced, the spatial resolution is still damaged, because only emission electrons are used for signals in the prior art. On the other hand, not the emission electrons, but changes in the tunneling current itself produced by stepping the high-brilliance monochromatic X-ray energy to be input to the sample 30 over the absorption edge of a specified element are measured in the scanning probe microscope system 10. As a result, it becomes possible to implement the condition/composition analysis on the surface of a material with the spatial resolution of 1000 times higher than that of the prior art.

In addition, when the scanning probe microscope system 10 is used, the surface of a material is not only observed, but a local reaction is controlled by the use of both of probe bias and high-brilliance monochromatic X-ray excitation, whereby it becomes also possible to prepare a nanostructure.

Namely, according to the above-described scanning probe microscope system 10, it becomes possible to conduct the observation and the evaluation of the atom arrangement, the electronic state of atoms, the structure of the molecular arrangement and the like on the surface of the sample 30, or the constitution, the working or the operation and the like of the nanostructure on the surface of the sample 30 while identifying elements.

It is to be noted that the above-described embodiment may be modified as described in the following paragraphs (1) through (5).

(1) In the above-described embodiment, although it is arranged in such that the sample 30 is moved with respect to the probe 22 and the incidence position of the beam of high-brilliance monochromatic X-rays, whereby the sample 30, the probe 22, and the incidence position of the beam of the high-brilliance monochromatic X-rays are moved relatively with each other, the invention is not limited thereto, as a matter of course. For example, it may be arranged in such that the probe 22 is moved with respect to the sample 30 and the incidence position of the beam of high-brilliance monochromatic X-rays, whereby the sample 30 and the probe 22 are moved relatively; or it may be arranged in such that the probe 22, the sample 30, and the incidence position of the beam of high-brilliance monochromatic X-rays are moved relatively with each other, whereby the sample 30, the probe 22, and the incidence position of the beam of the high-brilliance monochromatic X-rays are moved relatively.

(2) In the above-described embodiment, although it is arranged in such that the aperture member 42a is provided with the six pinholes 42a-1, 42a-2, 42a-3, 42a-4, 42a-5, and 42a-6, whereby it is possible to implement positioning operation ranging from rough positioning to high accurate positioning, the invention is not limited thereto as a matter of course, but the number of the pinholes to be provided on the aperture member may be an arbitrary number of one or more.

(3) In the above-described embodiment, although the case wherein the beam diameter of the high-brilliance monochromatic X-rays to be input to the sample 30 is made to be φ10 μm is illustrated, the invention is not limited thereto as a matter of course, but a smaller diameter than that of the prior art, i.e. a smaller diameter than 1 mm, e.g. any beam diameter from 1 μm or more to 100 μm or less may be suitably selected.

(4) In the above-described embodiment, it has been described that the scanning probe microscope system 10 is preferably operated in ultra-high vacuum environment. As described above, when the scanning probe microscope system 10 is operated in the ultra-high vacuum environment, the extra emission of electrons can be suppressed around the probe 22. Accordingly, the S/N ratio of signals can be improved. However, the environment for operating the scanning probe microscope system 10 is not limited to the ultra-high vacuum environment as a matter of course, but the scanning probe microscope system 10 may be operated in an environment other than the ultra-high vacuum environment dependent on a measurement object.

(5) The above-described embodiment may be suitably combined with the above-described modified examples in the paragraphs (1) to (4).

INDUSTRIAL APPLICABILITY

The present invention may be applied to the observation and the evaluation of an atom arrangement, an electronic state of atoms, the structure of a molecular arrangement and the like on the surface of a sample, and further, the invention is applicable to the constitution, the working or the operation and the like of the nanostructure on the surface of a sample.

The invention claimed is:

1. A scanning probe microscope system, comprising:
   an X-ray irradiation means for irradiating a measurement object with high-brilliance monochromatic X-rays having a beam diameter smaller than 1 mm at an acute angle to the object to establish a total reflection condition; and
   a scanning probe microscope having a probe arranged with respect to said measurement object in a tunneling condition,
   a processing means for detecting and processing a tunneling current through said probe,
   an alignment means for relatively moving said measurement object, said probe, and the incident position of said high-brilliance monochromatic X-rays to the measurement object; and
   a fluorescent crystal screen having a density to permit observation of the interior of a region of the measurement object.

2. The scanning probe microscope system as claimed in claim 1, further comprising means to step the high-brilliance monochromatic x-rays over the absorption edge of a desired element.

3. the scanning probe microscope system as claimed in any one of claim 1 or 2, characterized in that:
   the beam diameter of the high-brilliance monochromatic X-rays irradiated form said X-ray means is 1 μm or more to 100 μm or less.

4. The scanning probe microscope system as claimed in claim 1, further comprising:
   X-ray irradiation means adapted to irradiate the high-brilliance monochromatic X-rays in total reflection condition with respect to said measurement object.

5. The scanning probe microscope system as claimed in claim 1, characterized in that said alignment means includes:
   a θ-stage having the rotating plane parallel to the horizontal plane in an XYZ-orthogonal coordinate system to control the incidence angle of the high-brilliance monochromatic X-rays irradiated from said X-ray irradiation means with respect to said measurement object,
   an Xt-stage for controlling the movement towards an X-axial direction in the XYZ-orthogonal coordinate system to match the extreme end of said probe with the rotating center of said .theta.-stage,
   a Zt-stage for controlling the movement towards a Z-axial direction in the XYZ-orthogonal coordinate system to match the extreme end of said probe with the rotating center of said .theta.-stage,
   a Zb-stage for controlling the movement towards the Z-axial direction in the XYZ-orthogonal coordinate system to match said rotating center of the .theta.-stage with the beam position of the high-brilliance X-rays irradiated from said X-ray irradiation means, and
   a Yb-stage for controlling the movement towards the Y-axial direction in the XYZ-orthogonal coordinate system to match the height of an observation point of said measurement object immediately below said probe with the beam position of the high-brilliance monochromatic X-rays.

6. The scanning probe microscope system as claimed in claim 1, characterized by:
including further a monitoring means for monitoring the vicinities of an observation point on said measurement object immediately below said probe.

7. The scanning probe microscope system as claimed in claim 6, characterized in that said monitoring means includes:
an aperture member positioned at the uppermost stream with respect to the beam traveling direction of the high-brilliance monochromatic X-rays irradiated from said X-ray irradiation means and provided with at least one pinhole for reducing the beam diameter to a diameter smaller than 1 mm
an ion chamber for monitoring the beam intensity of the beam of the high-brilliance monochromatic X-rays passed through the pinhole of said aperture member,
an absorption plate for absorbing the high-brilliance monochromatic X-rays irradiated to said measurement object to decrease the beam intensity,
the fluorescent crystal screen, to which the high-brilliance monochromatic X-rays passed through said absorption plate are irradiated, whereby the positional relationship among said probe, said measurement object, and the beam position of said high-brilliance monochromatic X-rays is projected on the screen in the form of a shadowgraph,
an optical microscope system for amplifying said shadowgraph projected on the screen,
a CCD camera for taking the shadowgraph amplified by said optical microscope system,
a reflecting mirror for reflecting said shadowgraph on the screen to input to said CCD camera, and a semiconductor analyzer for counting the yield point of the fluorescence X-rays emitted from said measurement object and said probe to analyze the energy.

8. The scanning probe microscope system as claimed in claim 1, characterized in that said probe is coated with an insulating material other than at an extreme end thereof.

9. The scanning probe microscope system as claimed in claim 1, characterized in that said probe comprises a carbon nanotube.

10. The scanning probe microscope system as claimed in claim 1, further comprising means for providing an ultra-high vacuum environment for operating the system.

11. The system of claim 4, wherein the beam is incident on the measurement object at an angle incidence of approximately 0.1°.

12. The system of claim 1, wherein the high-brilliance monochromatic X-rays have a beam diameter of about 10 microns.

* * * * *